US008428961B2

(12) United States Patent
Greischar et al.

(10) Patent No.: US 8,428,961 B2
(45) Date of Patent: *Apr. 23, 2013

(54) METHOD AND SYSTEM FOR DATA AGGREGATION FOR REAL-TIME EMERGENCY RESOURCE MANAGEMENT

(75) Inventors: Patrick J. Greischar, Whitefish Bay, WI (US); Edward Barthell, Mequon, WI (US); Robert Hedgcock, Oconomowoc, WI (US); Elaine Schweitzer, Whitefish Bay, WI (US); David R. Colwell, Pewaukee, WI (US); Chris Felton, Menomonee Falls, WI (US)

(73) Assignee: EMSystem, LLC, Milwaukee, WI (US)

( * ) Notice: Subject to any disclaimer, the term of this patent is extended or adjusted under 35 U.S.C. 154(b) by 1184 days.

This patent is subject to a terminal disclaimer.

(21) Appl. No.: 11/895,705

(22) Filed: Aug. 27, 2007

(65) Prior Publication Data
US 2007/0297589 A1   Dec. 27, 2007

Related U.S. Application Data

(63) Continuation-in-part of application No. 11/506,850, filed on Aug. 18, 2006, and a continuation-in-part of application No. 11/226,875, filed on Sep. 14, 2005.

(51) Int. Cl.
*G06Q 10/00* (2012.01)
(52) U.S. Cl.
USPC ........................................ 705/2; 705/3; 705/5
(58) Field of Classification Search .................. 379/201, 379/201.01; 702/5; 705/5, 8, 2–3; 707/2, 707/3
See application file for complete search history.

(56) References Cited

U.S. PATENT DOCUMENTS

| 5,301,105 A | 4/1994 | Cummings, Jr. |
| 5,454,024 A | 9/1995 | Lebowitz |

(Continued)

FOREIGN PATENT DOCUMENTS

| JP | 2002-358371 | 12/2002 |
| JP | 2003-067502 | 3/2003 |

(Continued)

OTHER PUBLICATIONS

HAvBED System, Public health preparedness, Agency for Healthcare Research and Quality (www.ahrg.gov/prep/havbed) Appendix D; Preliminary System Specification Document, Version Jan. 21, 2005.

(Continued)

*Primary Examiner* — Disler Paul
(74) *Attorney, Agent, or Firm* — Foley & Lardner LLP

(57) ABSTRACT

A system and method for providing information about resource availability, especially during an emergency such as a natural disaster, is herein proposed. The system stores resource information about multiple facilities, across cities, counties, states and even countries. Such information can be provided to designated users based on specified access levels for the user and the resource information. Further, the system is able to exchange the resource availability information with external systems and databases. The resource information is also automatically updated to reflect the most current information. The system is useful in directing resources to participate in an emergency. Further the system aggregates resource information based on one or more attributes, such as region, hospital, city, state, etcetera, that is associated with the resource information.

27 Claims, 8 Drawing Sheets

U.S. PATENT DOCUMENTS

| | | | |
|---|---|---|---|
| 5,558,638 A * | 9/1996 | Evers et al. | 604/66 |
| 5,911,687 A | 6/1999 | Sato et al. | |
| 5,945,919 A | 8/1999 | Trask | |
| 6,014,629 A * | 1/2000 | DeBruin-Ashton | 705/2 |
| 6,055,506 A | 4/2000 | Frasca, Jr. | |
| 6,088,679 A | 7/2000 | Barkley | |
| 6,117,073 A | 9/2000 | Jones et al. | |
| 6,212,393 B1 | 4/2001 | Suarez et al. | |
| 6,305,605 B1 | 10/2001 | Goetz et al. | |
| 6,377,210 B1 | 4/2002 | Moore | |
| 6,499,658 B2 | 12/2002 | Goetz et al. | |
| 6,560,569 B1 | 5/2003 | Abu El Ata | |
| 6,563,910 B2 | 5/2003 | Menard et al. | |
| 6,567,796 B1 * | 5/2003 | Yost et al. | 1/1 |
| 6,571,285 B1 | 5/2003 | Groath et al. | |
| 6,574,480 B1 | 6/2003 | Foladare et al. | |
| 6,594,634 B1 | 7/2003 | Hampton et al. | |
| 6,701,156 B2 | 3/2004 | Akhteruzzaman et al. | |
| 6,761,312 B2 | 7/2004 | Piatek et al. | |
| 6,789,046 B1 | 9/2004 | Murstein et al. | |
| 6,957,218 B1 | 10/2005 | Wyatt | |
| 6,975,963 B2 | 12/2005 | Hamilton et al. | |
| 7,001,334 B2 | 2/2006 | Reed et al. | |
| 7,034,678 B2 | 4/2006 | Burkley et al. | |
| 7,177,623 B2 | 2/2007 | Baldwin | |
| 7,200,207 B2 | 4/2007 | Meer et al. | |
| 7,337,146 B2 | 2/2008 | Heelan et al. | |
| 7,661,146 B2 | 2/2010 | Karimzadeh et al. | |
| 7,890,341 B2 | 2/2011 | McNally et al. | |
| 7,899,682 B2 | 3/2011 | Sacco et al. | |
| 8,010,386 B2 | 8/2011 | Wyatt | |
| 2001/0032195 A1 | 10/2001 | Graichen et al. | |
| 2002/0011518 A1 | 1/2002 | Goetz et al. | |
| 2002/0013714 A1 * | 1/2002 | Dubler et al. | 705/2 |
| 2002/0032593 A1 * | 3/2002 | Berman | 705/8 |
| 2002/0153413 A1 | 10/2002 | Piatek et al. | |
| 2002/0198445 A1 | 12/2002 | Dominguez et al. | |
| 2003/0021417 A1 | 1/2003 | Vasic et al. | |
| 2003/0040939 A1 | 2/2003 | Tritch et al. | |
| 2003/0074222 A1 | 4/2003 | Rosow et al. | |
| 2003/0115085 A1 * | 6/2003 | Satoh | 705/5 |
| 2003/0177051 A1 | 9/2003 | Driscoll et al. | |
| 2003/0212494 A1 * | 11/2003 | Alexander et al. | 702/5 |
| 2004/0006492 A1 | 1/2004 | Watanabe | |
| 2004/0070515 A1 | 4/2004 | Burkley et al. | |
| 2004/0138925 A1 * | 7/2004 | Zheng | 705/2 |
| 2004/0153343 A1 | 8/2004 | Gotlieb et al. | |
| 2004/0153440 A1 * | 8/2004 | Halevy et al. | 707/3 |
| 2004/0162707 A1 | 8/2004 | Saint-Amour et al. | |
| 2004/0193447 A1 | 9/2004 | Joseph | |
| 2004/0243446 A1 * | 12/2004 | Wyatt | 705/2 |
| 2005/0001720 A1 | 1/2005 | Mason et al. | |
| 2005/0010436 A1 | 1/2005 | Merkin | |
| 2005/0038696 A1 | 2/2005 | Kalevik et al. | |
| 2005/0055330 A1 | 3/2005 | Britton et al. | |
| 2005/0075904 A1 | 4/2005 | Wager et al. | |
| 2005/0131740 A1 | 6/2005 | Massenzio et al. | |
| 2005/0137929 A1 | 6/2005 | Frazier et al. | |
| 2005/0201345 A1 | 9/2005 | Williamson | |
| 2005/0201359 A1 | 9/2005 | Nelson et al. | |
| 2005/0201528 A1 | 9/2005 | Meer et al. | |
| 2005/0201529 A1 | 9/2005 | Nelson et al. | |
| 2005/0282141 A1 | 12/2005 | Falash et al. | |
| 2006/0235716 A1 | 10/2006 | Mahesh et al. | |
| 2006/0235936 A1 | 10/2006 | Lei et al. | |
| 2006/0236247 A1 | 10/2006 | Morita et al. | |
| 2006/0277595 A1 | 12/2006 | Kinser et al. | |
| 2007/0021981 A1 | 1/2007 | Cox | |
| 2007/0061393 A1 | 3/2007 | Moore | |
| 2007/0078677 A1 | 4/2007 | Hofstetter | |
| 2007/0239484 A1 * | 10/2007 | Arond et al. | 705/2 |
| 2007/0280462 A1 | 12/2007 | Neece | |
| 2007/0285226 A1 | 12/2007 | Yi | |

FOREIGN PATENT DOCUMENTS

| | | |
|---|---|---|
| JP | 2003-091597 | 3/2003 |
| JP | 2003-111735 | 4/2003 |
| JP | 2003-224674 | 8/2003 |
| JP | 2007-334893 | 12/2003 |
| JP | 2005-174111 | 6/2005 |
| JP | 2006-167400 | 6/2006 |
| JP | 2007-094459 | 4/2007 |
| JP | 2007-141245 | 6/2007 |
| JP | 2008-178651 | 8/2008 |

OTHER PUBLICATIONS

Comcare emergency response alliance web page, HAVE (hospital availability exchange), (www.comcare.org/HAVE).

HAvBED System, Section IV. Methods; (www.ahrg.gov/prep/havebed).

Onji, Y., "EMS communication system in Osaka, Japan", *JACEP*, 6(7), pp. 312-314; Jul. 1977.

Neely, KW, et al., "Computerized Hospital On-Line Resources Allocation Link (CHORAL): A Mechanism to Monitor and Establish Policy for Hospital Ambulance Diversions", *Prehospital Disaster Med.*; 6(4), pp. 459-462, Oct.-Dec. 1991.

US Department of Justice, Crisis Information Management Software (CIMS) Feature Comparison Report, Oct. 2002.

EIC Comcare Press Release, "EIC and Comcare Announce Submission of Draft Hospital Emergency Resource Standard to OASIS," EIC Comcare Emergency Response Alliance, Jan. 23, 2006, 2 pages.

Non-final Office Action received for U.S. Appl. No. 11/506,850 dated Mar. 2, 2010.

Non-final Office Action received for U.S. Appl. No. 11/728,357 dated Mar. 3, 2010.

Final Office Action on U.S. Appl. No. 11/226,875 dated Nov. 9, 2009.

U.S. Non-Final Office Action, dated: Feb. 15, 2011; In re: U.S. Appl. No. 11/226,875, (15 pgs.).

Barthell, et al., "Assuring community emergency care capacity with collaborative internet tools: the Milwaukee Experience," Journal of Public Health Management and Practice; Jan./Feb. 2003; vol. 9, Issue 1, pp. 35-42.

Final Office Action received for U.S. Appl. No. 11/226,875 dated Sep. 14, 2010.

Final Office Action received for U.S. Appl. No. 11/506,850 dated Aug. 3, 2010.

Final Office Action received for U.S. Appl. No. 11/728,357 dated Aug. 3, 2010.

Final Office Action received for U.S. Appl. No. 12/243,860 dated Oct. 13, 2010.

Non-final Office Action issued in U.S. Appl. No. 12/243,860 mailed Aug. 20, 2009.

Final Office Action issued in U.S. Appl. No. 12/243,860 mailed Oct. 23, 2009.

Non-final Office Action received for U.S. Appl. No. 12/243,860 dated Jul. 28, 2010.

Non-final Office Action received for U.S. Appl. No. 11/226,875 dated May 10, 2010.

Final Office Action; Dated: Jul. 12, 2011; in re U.S. Appl. No. 11/226,875; Applicant: Patrick J. Greischar; (17 pgs.).

Foldy, Seth L. MD, et al.; "The Public Health Dashboard: A Surveillance Model for Bioterrorism Preparedness"; Journal of Public Health Management & Practice, (May/Jun. 2004); vol. 10, No. 3, (Abstract Only) (1 pg.).

Non-Final Office Action; Dated: Jun. 27, 2011; in re U.S. Appl. No. 12/243,860; Applicant: Patrick J. Greischar; (15 pgs.).

Final Office Action; Dated: Aug. 23, 2011; in re U.S. Appl. No. 12/243,860; Applicant: Patrick J. Greischar; (14 pgs.).

US Advisory Action; Dated: Sep. 19, 2011; in re U.S. Appl. No. 11/226,875; Applicant: Patrick J. Greischar; (3 pgs.).

Non-final Office Action received in U.S. Appl. No. 11/728,357 dated Aug. 27, 2012 (27 pages).

Final Office Action issued in U.S. Appl. No. 11/728,357 mailed Jan. 16, 2013 (22 pages).

\* cited by examiner

Figure 8

HAvBED EDXL Communication Schema

```xml
<?xml version="1.0" ?>
<xs:schema xmlns:xs="http://www.w3.org/2001/XMLSchema"
    targetNamespace="http://www.statusmessage.org/ns/hospital/v1.0"
    xmlns:rs="http://www.statusmessage.org/ns/hospital/v1.0"
    xmlns:core="http://www.statusmessage.org/ns/coredomain/v1.0">
<xs:import namespace="http://www.statusmessage.org/ns/coredomain/v1.0"
    schemaLocation="CoreDomain.xsd"/>
    <xs:element name="hospitalStatus">
        <xs:annotation>
            <xs:documentation>Communicate the status of one or more
hospitals.</xs:documentation>
        </xs:annotation>
        <xs:complexType>
            <xs:sequence>
                <xs:element name="hospital" maxOccurs="unbounded">
                    <xs:complexType>
                        <xs:sequence>
                            <xs:element name="id" type="xs:string">
                                <xs:annotation>
                                    <xs:documentation>Unique identifier for this
hospital.</xs:documentation>
                                </xs:annotation>
                            </xs:element>
                            <xs:element name="hospitalName" type="xs:string" minOccurs="0"/>
                            <xs:element name="location" type="xs:string" minOccurs="0"/>
                            <xs:element name="emergencyDepartment"
    type="rs:EmergencyDepartment" minOccurs="0"/>
                            <xs:element name="hospitalBedCapacity"
    type="rs:HospitalBedCapacity" minOccurs="0"/>
                            <xs:element name="physicianCoverage" type="rs:PhysicianCoverage"
    minOccurs="0"/>
                            <xs:element name="hospitalEOC" type="rs:HospitalEOC"
    minOccurs="0"/>
                            <xs:element name="ventilators" type="rs:Ventilators"
    minOccurs="0"/>
                            <xs:element name="comments" type="xs:string" minOccurs="0"/>
                            <xs:element name="updateTime" type="xs:dateTime"/>
                        </xs:sequence>
                    </xs:complexType>
                </xs:element>
            </xs:sequence>
        </xs:complexType>
    </xs:element>
```

METHOD AND SYSTEM FOR DATA AGGREGATION FOR REAL-TIME EMERGENCY RESOURCE MANAGEMENT

CROSS-REFERENCE TO RELATED APPLICATIONS

This non-provisional utility patent application claims the benefit of one or more prior filed co-pending non-provisional applications; a reference to each such prior application is identified by the relationship of the applications and application number (series code/serial number). The present application is a Continuation-In-Part of application Ser. No. 11/506,850, titled "Method and System for Real-Time Emergency Resource Management", filed on Aug. 18, 2006; and a Continuation-In-Part of application Ser. No. 11/226,875, titled "Electronic Data Management System for Emergency First-Responders and Method of Use", filed on Sep. 14, 2005 which are incorporated herein by reference in their entirety.

BACKGROUND OF THE INVENTION

1. Field of the Invention

The present invention relates generally to a resource management system for use by personnel managing an incident. Additionally, the present invention relates to a computer system and method for emergency personnel to efficiently collect, store, aggregate and manage availability information regarding resources and equipment according to the needs of the patients, evacuees, people or those injured.

2. Description of the Prior Art

A multiple-victim disaster or an emergency can overwhelm ill-prepared local or state officials. This is especially true if resources available to handle the disaster or the emergency are constrained. In the case of a medical disaster, disaster victims may be routed to medical facilities where the medical resources (number of available beds, facilities to treat a certain type of victims) are limited or already in use for treating similar victims from the same disaster location or another disaster location. In such a case, there may be other medical facilities that are equipped to accommodate the victims, but may be unutilized for a number of reasons, primarily lack of knowledge about the availability of resources at a facility.

Hence, there is a need for a system that tracks in real-time the availability of resources across multiple facilities in order to better direct victims of an emergency or disaster to these resources. Additionally, the system should be able to categorize these resources and the patients/victims needs so that it can better direct the patients/victims according to the type of resource required to treat the patient/victim. The system should also be able to track the availability of resources from multiple facilities across regions, cities and in certain cases across states. This system should be accessible at the emergency location or at multiple locations in case of a natural disaster to enable central tracking of the resources. The system should also support communication of resource status and availability across one or many users in the region, city, county, state or other response territory. Furthermore, this system should utilize common standards such that different facilities can use existing systems to connect to such a system and report their resource availability. This system should be able to collect availability information from a number of facilities and aggregate the data so that people responsible for managing the emergencies are provided with aggregated counts by cities, regions or other aggregation criterion.

One such system is described in U.S. Publication No. 20040138925, titled "Resources utilization management system and method of use". This patent application describes a resource utilization system that graphically depicts utilization levels of resources in a hospital. Examples of the different types of resources include beds, rooms as well as human resources such as medical staff, physicians, etc. The application further describes the method of managing these resources by first assigning these resources to subjects such as patients. During the assignment, the system displays the utilization of the resources giving an indication to the user about the availability of the resources.

U.S. Publication No. 20030074222, titled "System and method for Managing Patient Bed Assignments and Bed Occupancy in a Health Care Facility" describes a computer implemented system for managing the assignment of beds in a medical facility. The claimed system functions in conjunction with an admission/discharge/transfer system and keeps track of the beds in a medical facility and the assignment of beds to incoming patients. It also displays a real-time status of the beds available in the facility and the beds that are currently assigned to patients in the facility.

U.S. Publication No. 20040243446, titled "Method and a System for Optimizing Hospital Beds and Ambulance Allocations via a Computer Network" describes a computer based system that enables users to view the real-time status of beds available in a medical facility such as a hospital. Further, the system enables the hospital to communicate this status to an ambulance that is directing one or more patients to the hospital. If the hospital does not have the available capacity to accommodate the patients being transported in the ambulance, then the ambulance is redirected to a second facility or hospital.

From the above discussion, it is clear that there is a need for a system that will enable tracking availability of resources from multiple facilities. The system should also be able to list resources by type so that availability of a certain type of resource, such as, bed capacity by triage category is readily available. Additionally, the system should be able to gather resource availability information from different regional systems and medical facilities. It should be able to present this information at the time of emergency so that the information can be used to make better decisions.

SUMMARY OF THE INVENTION

A first aspect of the present invention is to provide a system for providing resource information to a user, the resource information comprising availability of resources in at least one facility in at least one region, the system including at least one database, the at least one database storing the resource information for at least one facility, an access control module for controlling access to the resource information stored in the database, at least one client for viewing the resource information, a resource interface module for collecting resource information from the at least one facility in the at least one region, and a data aggregation module for aggregating the collected resource information based on one or more attributes associated with the resource information, wherein the data aggregation module is operable to access the information on the at least one database.

A second aspect of the present invention is to provide a method for providing resource information to at least one user, the resource information comprising availability of resources associated with one or more facilities in one or more regions, the method including the steps of collecting resource availability information from at least two facilities, the resource availability information further comprising a region associated with the facility, storing the resource information in a database along with a timestamp identifying a date and time at which the information was collected, aggregating resource availability information by summing resource availability based on the region associated with each of the facilities, and providing the aggregated resource information to the at least one user.

It is yet another aspect of the present invention to provide a system for providing resource information to a user, the resource information comprising availability of resources in at least one facility in at least one region, the system including at least one database, the at least one database storing the resource information for at least one facility, an access control module for controlling access to the resource information stored in the database, at least one client for viewing the resource information, a first resource interface module for collecting resource information from the at least one facility in the at least one region, wherein the resource interface is a web service that connects to at least one HAVE compatible resource information data store over a network to collect resource information about the at least one facility, a second resource interface module for collecting resource information from the at least one facility in the at least one region, wherein the resource interface is a web portal that allows at least one second user to manually input resource information for the at least one facility in the at least one region, a data aggregation module for aggregating the collected resource information based on one or more attributes associated with the resource information, wherein the data aggregation module is operable to access the information on the at least one database, and a data exchange module for providing the aggregated resource information to a central repository, thereby providing gathering, aggregating, storing, and exchanging information to support regional or federal guidelines including HAVE guidelines and HAvBED specifications.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 8 is a schematic view of an exemplary XML schema for exchange of resource availability information, in accordance with an embodiment of the present invention.

DETAILED DESCRIPTION OF THE PREFERRED EMBODIMENTS

Figure 1:
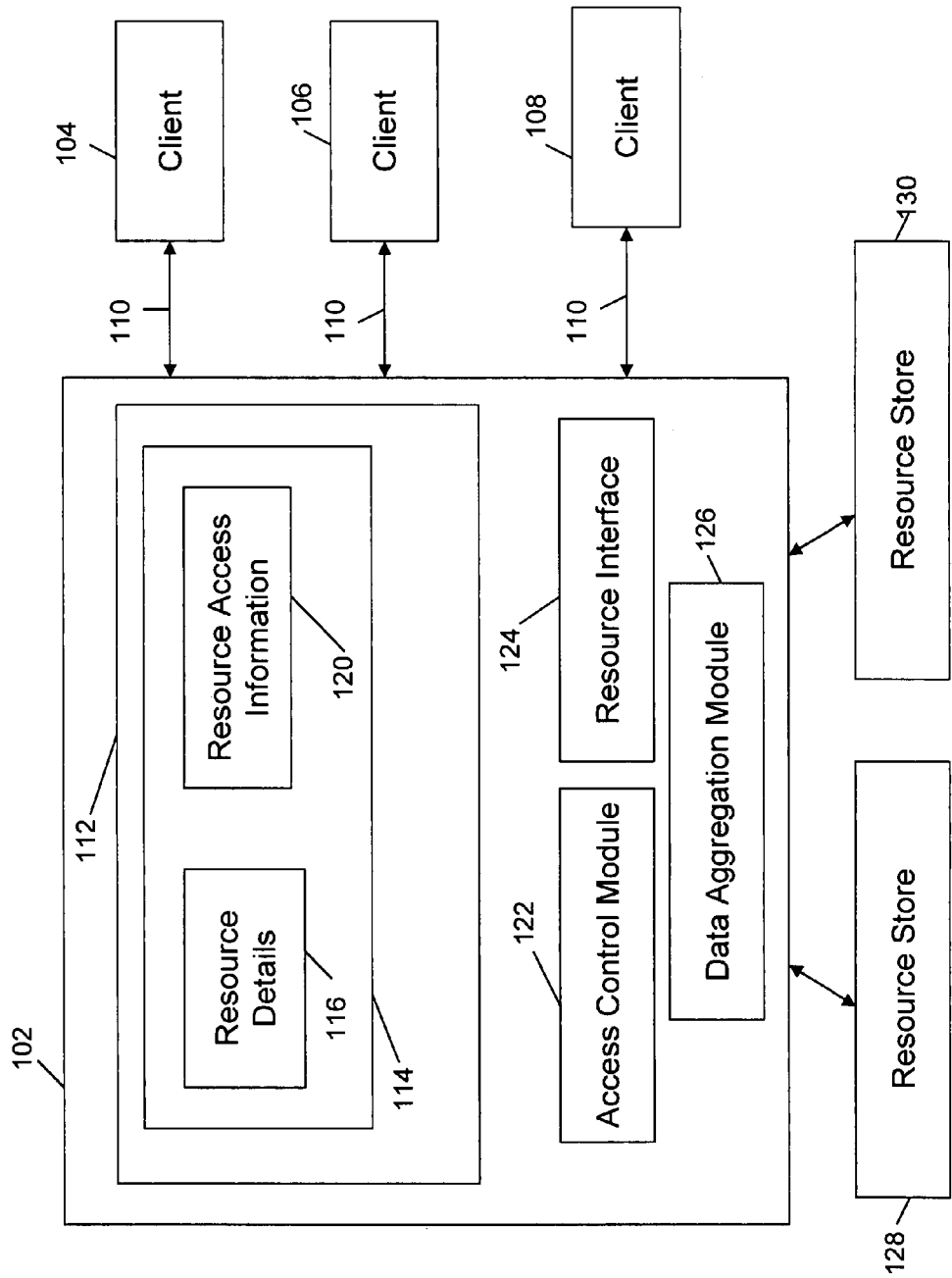
FIG. 1 is a schematic view of the overall system in accordance with an embodiment of the present invention.

The present invention provides a method and system for aggregating resource availability information collected from multiple facilities in one or more regions. The present system tracks medical and non-medical resource availability information by type and provides it to users requesting the information. The system collects availability information from individual hospitals and other medical facilities. This is enabled through a web interface that connects to the facilities and queries the availability data through industry standard techniques. There is an addition web interface that allows administration personnel to connect to the system and manually input the resource availability information. Furthermore, the system can also connect to central systems, such as those maintained by states, counties, etcetera to collect availability information.

Preferably the system is setup to collect the resource availability information at pre-determined time intervals; alternatively the time intervals are determined ad hoc or as needed. These intervals are user defined and can be changed/modified as per the user requirements. The system collects resource availability information, such as availability information about hospital beds, and stores this information in a database. This information is stored along with the time at which it was collected. This allows users who query the system to obtain the latest information along with the time at which it was obtained. This is important in emergencies, where personnel directing patients should have access to the latest information.

Resource information collected from individual medical facilities is stored in a database. A region that the medical facility is associated with is also stored along with the resource information. This region can be a city, county, state, or any other geographic region that can be used to aggregate data.

The system also allows for protecting the resource information, and the resource information is provided only to authorized users. Further, the users are only authorized to view resource information for certain specified resources. This enables the system of the present invention to restrict certain users from viewing resource information from resources that they are not authorized to view. Administrators of the system can define resources by region. Additionally, they can define the regions for which the users are authorized to view resource information. In certain special cases, the administrators can grant access to certain users to view resource information for regions for which the users are not initially authorized. This can be done on a per user basis, for a specified time frame or for a specified medical emergency or event.

The present invention provides for tracking of medical resources including but not limited to hospital beds, hospital rooms, Emergency Medical Services such as ambulance availability, medical personnel availability, availability of medical equipment such as defibrillators, decontamination facilities, negative pressure isolation rooms, ventilators, etc. These resources are tracked across one or multiple regions. A region can be defined as a part of a town or city, a town, city, county, state and even a country. The present invention also provides for tracking of non-medical resources including but not limited to shelters, vehicles, equipment, beds and other resources such as capacity in shelters, etc.

The present invention also provides a method and a system for interacting and exchanging resource information from other systems, such as Crisis Information Management System (CIMS), Computer Aided Dispatch system (CAD), Hospital Alert Network (HAN), etc.

The present invention also provides a method and a system for gathering, aggregating, storing, and exchanging information to support regional or federal guidelines including Hospital Availability Exchange (HAVE) guidelines (see "HAVE." COMCARE; available at http://www.comcare.org/HAVE-.html, herein incorporated by reference in its entirety) and Hospital Available Beds in Emergencies and Disasters (HAvBED) specifications (see "National Hospital Available Beds for Emergencies and Disasters (HAvBED) System: Final Report." AHRQ Publication No. 05-0103, December 2005. Agency for Healthcare Research and Quality, Rockville, Md.; available at http://www.ahrq.gov/research/havbed/, herein incorporated by reference in its entirety). The system allows users to update the status of the resources of one or more facilities that the users are associated with, and is capable of reporting resource availability in standard categories as defined by the standard, and report data back to state and federal systems in a standardized format, using one or more standardized interface methodologies. The system allows standard categories of resource availability information to be stored, accessed, and updated by authorized users.

Referring now to the drawings in general, the illustrations are for the purpose of describing a preferred embodiment of the invention and are not intended to limit the invention thereto. FIG. 1 is a schematic view of the overall system in accordance with an embodiment of the present invention. Server 102 is connected to multiple clients 104, 106 and 108 via network 110. Server 102 may be any personal computer having one or processing means, storage means and memory means, as commonly known in the art. Clients 104, 106 and 108 can be personal computers, laptop computers, tablet PCs, mobile phones and other devices known in the art capable of accessing a website or running a standalone application. Clients 104, 106 and 108 access server 102 via network 110. Network 110 can be a local intranet, the internet, and the means of access the server 102 may be wired, wireless or via a mobile network.

Server 102 has database 112 residing on it. Database 112 is a database having means for storing data and organizing data into tables. Commercial examples of database 112 include Microsoft® SQL Server and Oracle®. In another embodiment of the present invention, database 112 may be separate from server 102. Database 112 may be on a second server that is connected to server 102 by means commonly known in the art.

Database 112 stores resource information 114 for one or more resources. In one embodiment of the present invention, database 112 is with a part of CIMS. In another embodiment, database 112 includes data elements specified in the Hospital Availability Exchange (HAVE) guidelines and the Hospital Available Beds in Emergencies and Disasters (HAvBED) specifications. Resource information 114 further comprises resource details 116 and resource access information 120. Resource details 116 include location of resource (region, city, state), type of resource, availability information, timing information, contact information, etc. Resource access information 120 is used to determine if users can access resource details 116. It also determines if users can search for a resource based on resource details 116. In one embodiment of the present invention, resource access information 120 stores a list of regions to which the resource details 116 will be visible. In another embodiment of the present invention, resource access information 120 stores a list of users that can view resource details 116.

Server 102 further comprises access control module 122. Access control module screens clients 104, 106 and 108 access server 102 and provides access to resource details on the basis of the resource access information 120. When a client requests to view resource information, access control module 122 first determines if client has access to resource information by matching client information with resource access information 120. In another embodiment of the present invention, clients 104, 106 or 108, request to view a list of all available resources. Access control module 122 retrieves resource details 116 for all resources that have specified access to client 104 in their resource access information 120.

Server 102 also comprises resource interface 124 that interfaces and exchanges resource information with external sources, such as resource stores 128 and 130. Resource stores 128 and 130 are computer systems that store resource availability information for one or more medical facilities. Resource interface 124 connects to resource stores 128, 130 through a web interface application that allows resource interface to poll required information from resource clients. Medical facilities that do not have resource stores 128, 130 can also manually feed their resource information by connected to resource interface 124 via a standard web browser or a customized application running on a computing device at that medical facility. In a preferred embodiment, resource interface 124 can be configured to pull in resource information from multiple sources at predefined time intervals, e.g., hourly, daily, weekly, etc. In another embodiment, it can be configured to pull in information based on user requests or client requests. In a third embodiment, it can be configured to pull in information on the basis of change in resource information 114 or resource details 116. For example, if the resource level for a given resource changes, the change is automatically reflected in resource details 116 for that particular resource. In a fourth embodiment, the interface provides access to resource data for authorized systems. These outside systems may include CIMS, state and federal HAVE systems, Health Alert Networks, and other systems.

Server 102 further comprises data aggregation module 126. Data aggregation module 126 aggregates the resource availability information stored in database 112. Module 126 provides clients 104, 106, 108 with aggregated resource availability information by one or more attributes in resource details 116, such as region, when requested by the clients.

In another embodiment of the present invention, access control module 122 is not part of server 102, but is part of another server that can communicate with server 102 by means known in the art. In yet another embodiment of the present invention, resource interface 124 is not part of server 102, but is part of another server that can communicate with server 102 by means known in the art.

Figure 2:
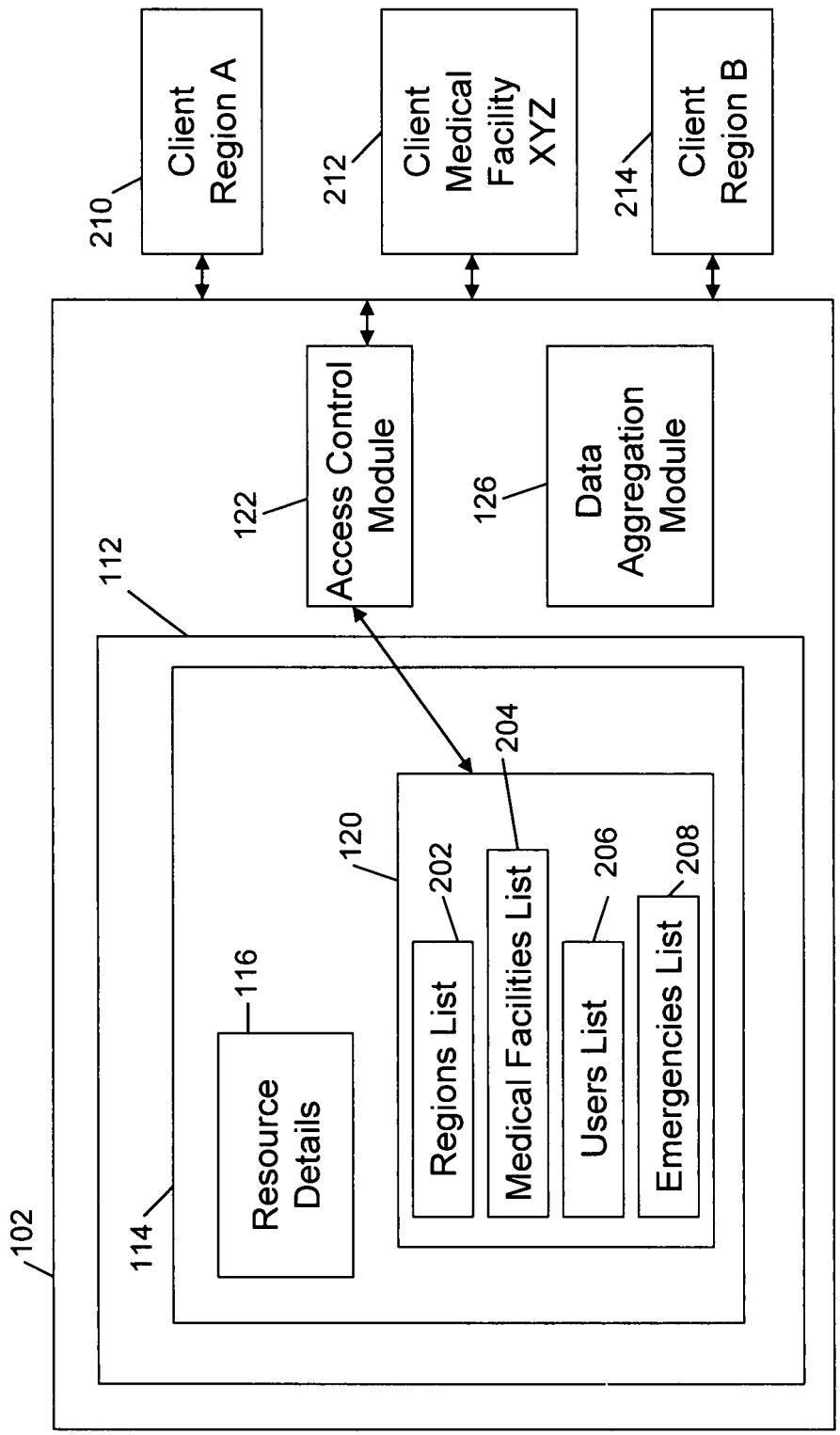
FIG. 2 is a schematic view of a system for providing clients with resource information, in accordance with an embodiment of the present invention.

FIG. 2 is a schematic view of a system for providing clients with resource information, in accordance with an embodiment of the present invention. Resource access information 120 further comprises regions list 202, medical facilities list 204, users list 206 and emergencies list 208. These lists specify regions, medical facilities, users and emergencies that can access resource details 116. A client 210 associated with region A tries to retrieve resource information for region B. The access control module 122 first determines the region of client 210. Next, access control module 122 retrieves a list of resources that have region A in their regions list 202 and belong to region B. This resource availability of these resources is then passed to client 210. In another embodiment of the present invention, client 212 associated with medical facility XYZ tries to retrieve availability information of one resource. The access control module 122 determines if that resource has medical facility XYZ in its medical facilities list 204. In case the medical facility is present in medical facilities list 204, resource details 116 for that resource are sent to client 212. In another embodiment, client 214 associated with region C requests resource information for resources in region C. The access control module 122 retrieves a list of resources in region C. In this case, access control module does not check to see if resources have given access to region C, since a client of region C requests to view resources of region C. In another embodiment, access control module 122 may first determine if the resources have region C in their regions list 202 before sending the resource information to client 214.

Figure 3:
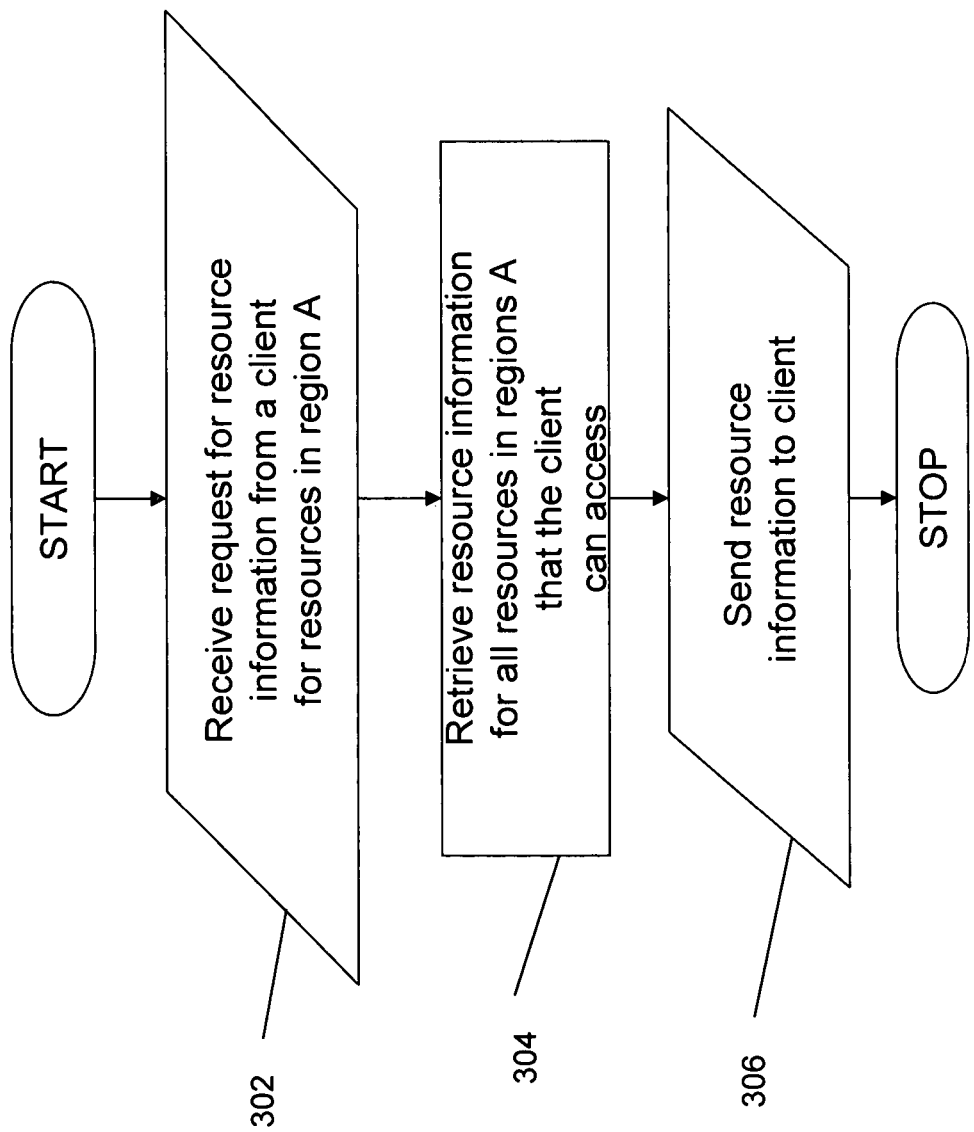
FIG. 3 is a flowchart depicting the steps of retrieving resource information of a region by a client associated with the same region, in accordance with an embodiment of the present invention.

FIG. 3 is a flowchart depicting the steps of retrieving resource information of a region by a client associated with the same region, in accordance with an embodiment of the present invention. A client that is associated with a given region sends a request to view resource information for the same region, in step 302. The system retrieves all resources that belong to that region and also have specified the same region in their regions list 202, in step 304. The resource information from all the retrieved resources is then sent to the client requesting the resource information, in step 306. In an embodiment of the present invention, the client requests resource information only for a certain type of resource. In this case, the resource information is filtered and only the requested resource information is forwarded to the client. In another embodiment of the present invention, the client only requests resource information from a single resource. In this case, the resource information for that resource is retrieved after verifying that the client has access to that resource information.

Figure 4:
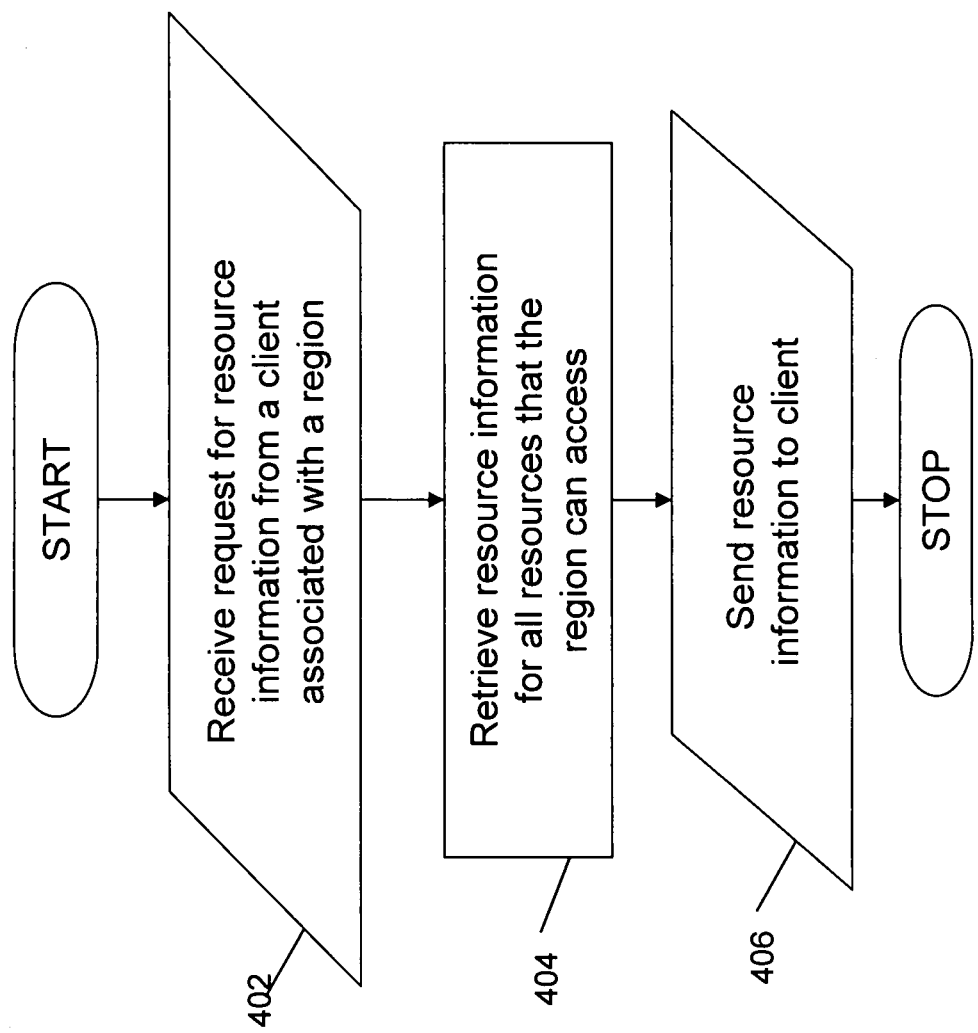
FIG. 4 is a flowchart depicting the steps of retrieving resource information of a region by a client associated with another region, in accordance with an embodiment of the present invention.

FIG. 4 is a flowchart depicting the steps of retrieving resource information of a region by a client associated with another region, in accordance with an embodiment of the present invention. A client that is associated with a given region sends a request to view resource information for another region, in step 402. The system retrieves all resources that belong to the second region and also have specified the first region in their regions list 202, in step 404. The resource information from all the retrieved resources is then sent to the client requesting the resource information, in step 406. In an embodiment of the present invention, the client requests resource information only for a certain type of resource. In this case, the resource information is filtered and only the requested resource information is forwarded to the client. In another embodiment of the present invention, the client only requests resource information from a single resource. In this case, the resource information for that resource is retrieved after verifying that the client has access to that resource information.

Figure 5:
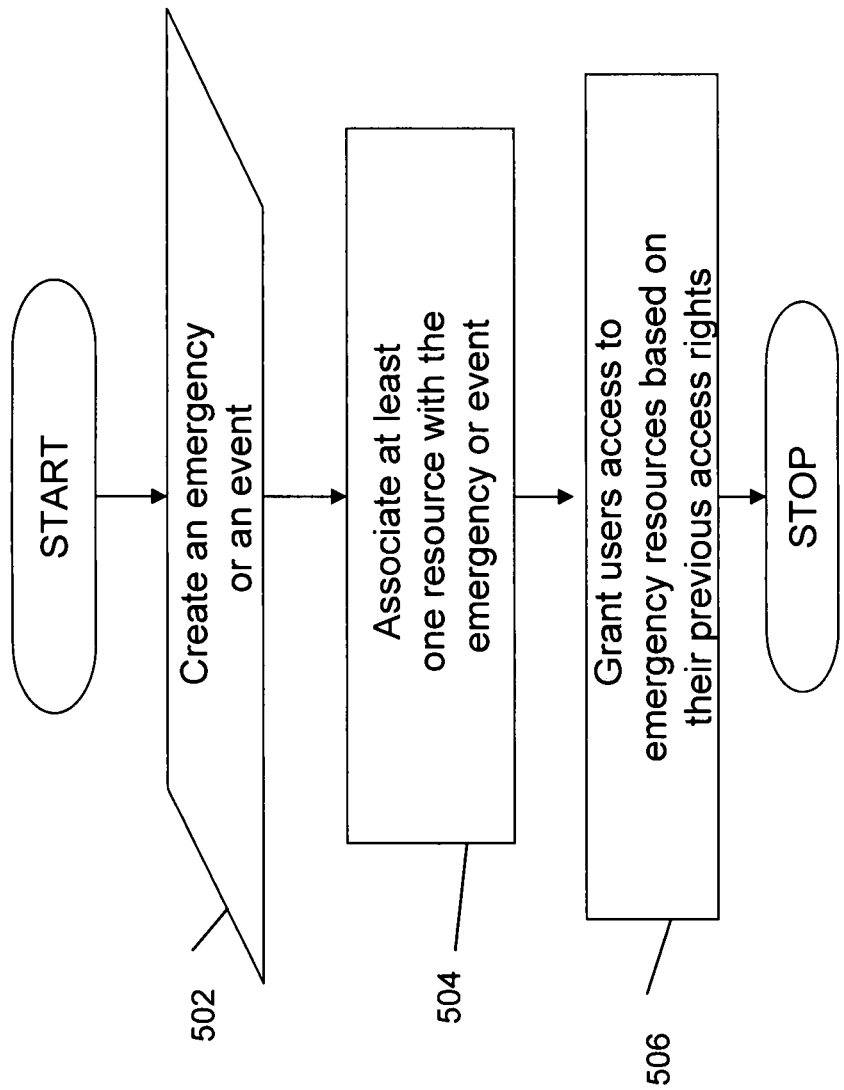
FIG. 5 is a flowchart depicting the steps involved in giving access to resource information to a user for a specific event, in accordance with an embodiment of the present invention.

FIG. 5 is a flowchart depicting the steps involved in giving access to resource information to a user for a specific event, in accordance with an embodiment of the present invention. First a supervisor needs to create an emergency or event in the system. This is depicted as step 502. Subsequently, the supervisor associates one or more resources with the emergency or event, at step 504. At step 506, the access rights of users are updated to provide access to the resources associated with the created emergency or event based on the users' previous access rights. In another embodiment of the present invention, instead of creating an emergency, the supervisor can specify a time frame for which the list of resources retrieved in step 506 will be available to a region, user or medical facility.

Figure 6:
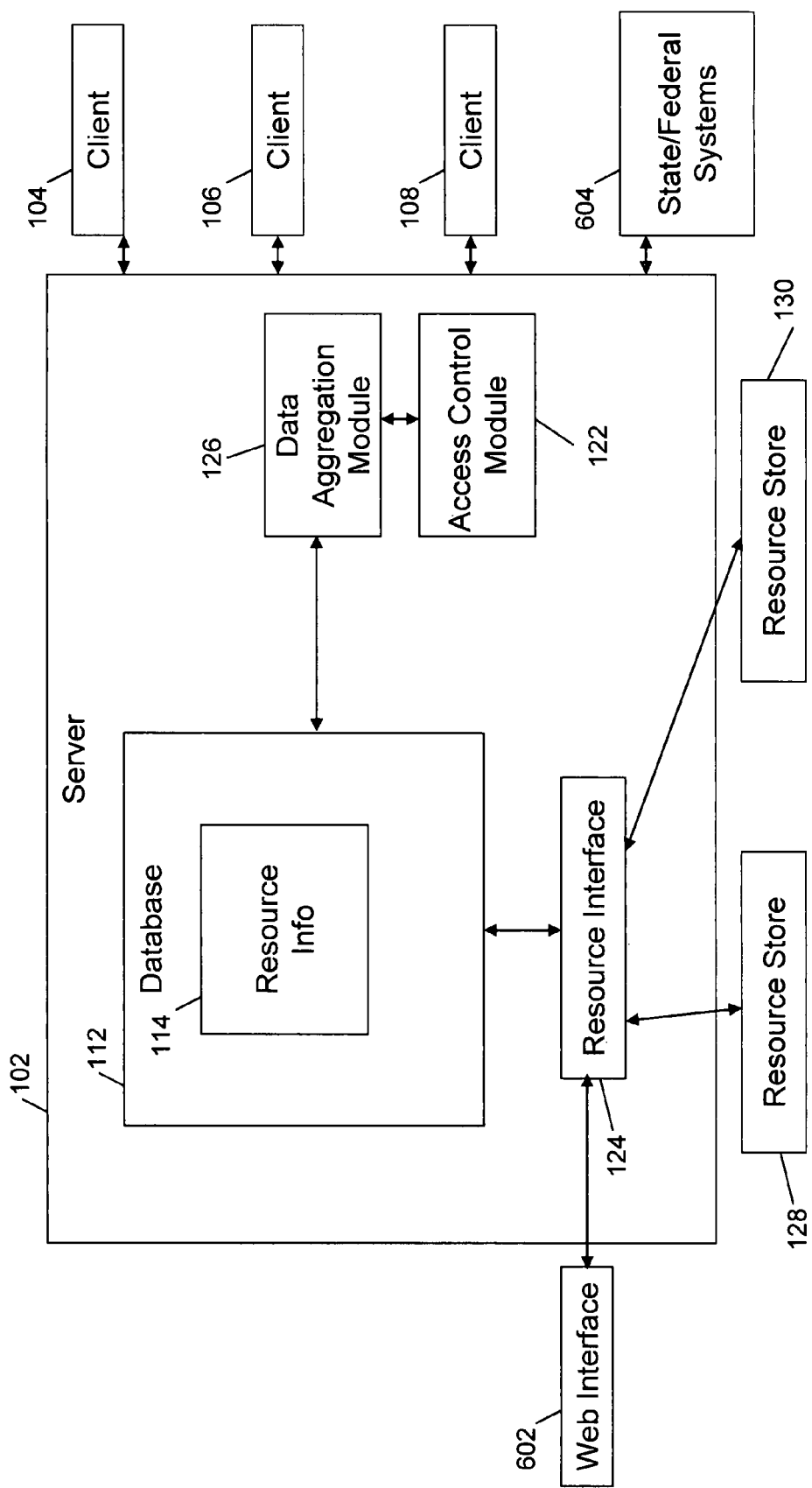
FIG. 6 is a schematic of the system for polling resource information from external resource stores and providing aggregated resource information to external users and databases, in accordance with an embodiment of the present invention.

FIG. 6 is a schematic of the system for polling resource information from external resource stores and providing aggregated resource information to external users and databases, in accordance with an embodiment of the present invention. Resource interface 124 connects with resource stores 128 and 130 to collect resource availability information. This information is stored in database 112 as resource information. Resource interface 124 preferably uses standard web service architecture to connect to resource stores 128 and 130. This process is similar to the web interface described above with the exception that the resource interface that is retrieving the resource availability information is authenticated using the web service. The same authorization module is used as with the web interface described above. The data is also aggregated in the same manner as described and is returned via an XML schema. In a preferred embodiment, resource stores 128 use standard XML schema to communicate data to resource interface 124. An example of this XML schema is the HAvBED EDXL Communication Schema. Resource interface 124 receives the data as an XML document, parses the document and stores the parsed data in database 112. Alternatively a non-web service interface could be utilized in place of the above described web interface.

Resource availability information is collected from multiple medical facilities and stored in database 112. The resource information comprises various fields, such as resource type (bed, room, emergency response vehicle), resource sub category (staffed bed, unstaffed bed, containment facility, etc), medical facility name, contact person and details, regional information (medical facility city, county and state, FEMA region, CDC region or other region types), and resource availability details such as number of resources available, time period of availability (immediate, in the next 24 hours, in the next 72 hours) and other related information. This information is stored along with a time and date at which it was recorded in database 112. Resource type can also be selected from the following list of hospital resource types: i. Intensive Care Unit (ICU), ii. Medical and Surgical (Med/Surge), iii. Burn Care, iv. Peds ICU, v. Pediatrics (Peds), vi. Psychiatric (Psych), vii. Negative Pressure Isolation, viii. Emergency Department Divert Status, ix. Decontamination Facility Available and x. Ventilators Available. This list is not meant to be exhaustive but is meant to illustrate the various types of resources on which availability data can be collected.

In a preferred embodiment, resource stores 128 and 130 store data that is compatible with Hospital Availability Exchange (HAVE) standards. Resource interface 124 collects resource information from resource stores 128 and 130 on a periodic basis. The time interval at which the information is collected is variable and can be modified as and when needed. It is typically 2 times per day, i.e., about every 12 hours.

As described above, information about region of a medical facility is stored along with the resource availability information. This region information is hierarchical in nature, which means that the facility can be identified by city, county, state, country or any other regional information such as FEMA region, CDC region. This allows for easy aggregation of availability data to a higher regional sum. A region could also be defined as a hospital system, such as those prevalent in metropolitan areas.

Some medical facilities, that may not have resource stores capable of communicating with resource interface 124, may use a web interface 602 provided by resource interface 124 to input resource availability information for their facility.

Administrative or other personnel from these facilities connect to the web interface, provide login credentials assigned to them, and input information for their respective facility. This information is then stored in database 112.

In case of large scale emergencies, multiple casualty incidents and disasters, it is desirable for emergency response coordinators to obtain resource availability information from regions that are close to the location of the emergency or disaster. These personnel or others who desire to obtain aggregated resource information connect to server 102 through clients 104, 106 or 108. Clients need to provide a login and password to be able to connect to server 102. Once connected, they can request aggregated resource data from data aggregation module 126. Data aggregation module 126 first verifies if the user requesting aggregated data has sufficient rights to access the data. This is carried out in a manner similar to that for providing resource data to clients, as shown in FIG. 2. Hence, access control module uses a mechanism similar to resource access information 120 to determine if a user can view the requested aggregated data. In an embodiment, information similar to resource access information 120 is maintained for each user that can login to the server 102. This is compared to the request for aggregated information to determine if the user can view the requested aggregated information. The user may request aggregated information by a region such as a state, city, county, or other region type (eg. FEMA region II which comprises the states of New Jersey and New York). Data aggregation module then queries database 112 for the requested information and sums resource availability counts for the latest available information by resource type to provide aggregated counts for each resource type available in those regions, based on the latest available data. In another case, client requesting such information may be only interested in a certain resource type. Hence, data aggregation module would only query database 112 for that specific resource type and aggregate data on this basis. It will be apparent to one skilled in the art that there are many different ways of aggregating data and querying data. This invention is not limited to the aggregation methods described above and is applicable to those other aggregations, which have been left out for the sake of brevity and readability.

In an alternate embodiment of the present invention, a state or federal resource availability system 604 can connect to server 102 to request aggregated resource availability information. The system 604 requests resource availability information via XML, using a predefined XML schema such as HAvBED EDXL Communication Schema. Data aggregation module 126 queries database 112 and parses the data into the same schema and sends the data as XML to system 604. In a preferred embodiment of the present invention, system 604 polls server 102 for aggregated data at fixed time intervals, such as every 12 hours.

Figure 7:
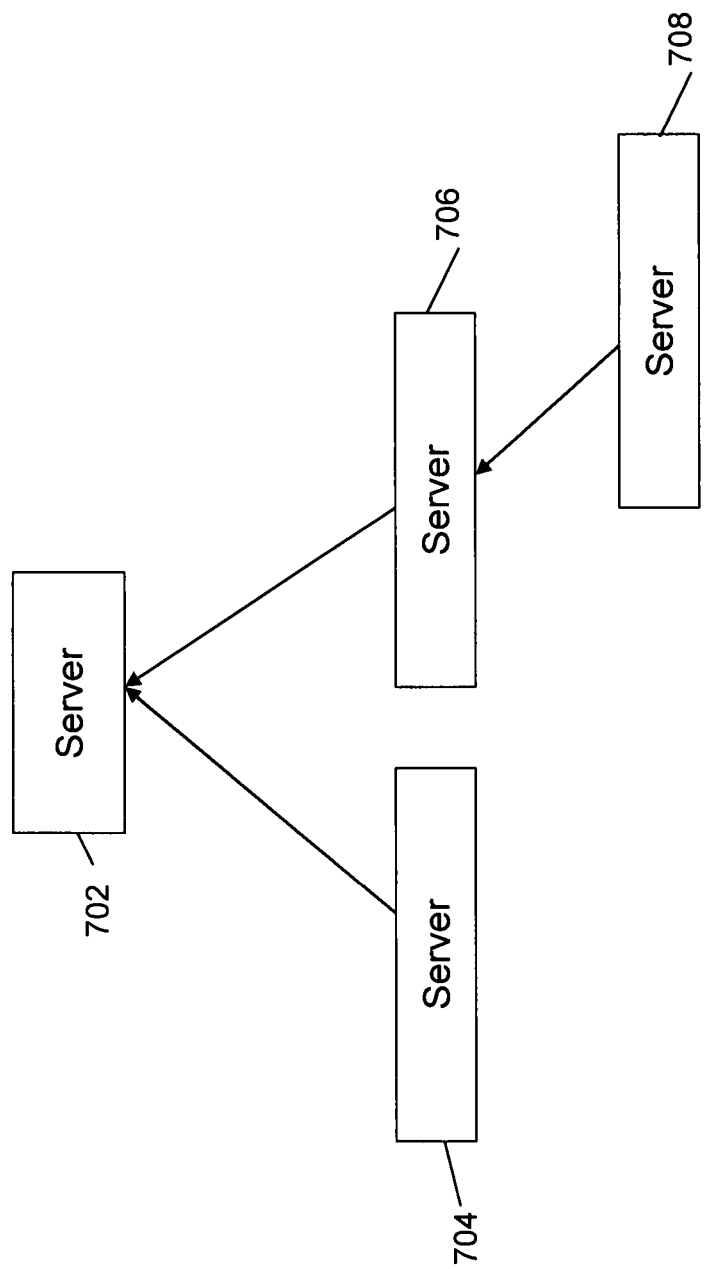
FIG. 7 is a schematic view of the system for communicating with external state and federal resource databases, in accordance with an embodiment of the present invention.

FIG. 7 is a schematic view of the system for communicating with external state and federal resource databases, in accordance with an embodiment of the present invention. FIG. 7 shows server 702, which preferably functions as a central repository, that is connected to two servers 704 and 706. Server 706 is in turn connected to server 708. Servers 702, 704, 706 and 708 have the same functionality as server 102, as described in FIG. 6. Alternatively, the information for the regions (e.g. external state and federal resources) may be stored in the same physical server or in the same database. Servers 704, 706 and 708 each are also connected to multiple resource stores that are not shown in the figure. Servers 704, 706 and 708 each also have a web interface that is also not shown in FIG. 7. In an exemplary embodiment, server 702 is a federal resource information server that provides resource availability information at a federal level (aggregated by state, FEMA region or other federal region). Server 702 uses the resource interface of the server to collect state level resource availability data from servers 704 and 706 (and other state resource servers not shown in the figure). Hence server 702 acts as a federal resource availability system 604 for servers 704 and 706. Servers 704 and 706 aggregate data at state level from resource stores and other local medical facilities and hospitals. Server 706 also connects to server 708, which runs at a county or city level. Hence, server 708 aggregates information at a city or county level by collecting resource availability information from all medical facilities in the city/county. Resource stores can be other similar systems that store resource information. In an embodiment, resource stores are CIMS or HAN system. In an embodiment, federal or state systems 604 are compatible with HAVE standards. Resource interface connects to the servers 704 and 706 via a network, such as the internet. The systems return data on the basis of the query sent and this data is stored in database 112.

In an embodiment of the present invention, the system is configured to derive performance metrics from the aggregated resource availability information. The performance metrics are user customizable, and are automatically generated by the data aggregation module based on the user specified schedule. Examples of metrics are metrics that show a percentage of hospitals that can report resource availability data within an hour, percentage of state emergency operation centers that can report bed availability within four hours of an emergency event.

In an embodiment of the present invention, users of the system are provided with modify and update rights for the stored resource information. These-rights are assigned to the users on the basis of the medical facility or region with which they are associated, similar to which access rights to the users are assigned.

Certain modifications and improvements will occur to those skilled in the art upon a reading of the foregoing description. Also, the resource management system is operable for use by first-alert responders to a medical crisis scene for coordinating patient-related data with resource-related data for optimizing system utilization and for making decisions regarding directing and transporting patients to suitable medical facilities having capabilities and capacity for treating each patient, wherein the system provides for use "on-site" of a disaster, accident, or location of a patient or at a medical facility.

The system enables the monitoring of resource availability information at a central location (such as by city, county, state or federal authorities). The system also provides for gathering resource availability information for mass casualty movement that may be required during large scale disasters and emergencies. It is also useful when trying to allocate patients to facilities that have appropriate capabilities to handle the patients (burn units, de-contamination, etc). In case of large scale disasters or emergencies, the system of the present invention us useful in determining the capacity of facilities in regions in and around the disaster or emergency.

All modifications and improvements have been deleted herein for the sake of conciseness and readability but are properly within the scope of the following claims.

What is claimed is:

1. A method of providing resource availability information related to medical facilities to a second device, the method comprising, at a first device:
    collecting resource availability information from a plurality of medical facilities, wherein the collecting the resource availability information comprises selectively polling, by the first device, one or more resource stores associated with the plurality of medical facilities, wherein the selectively polling the one or more resource stores associated with the plurality of medical facilities is performed:
  in response to the received resource availability query from the second device,
  periodically according to a user-defined schedule, or
  automatically in response to a change in the resource availability information;
storing the collected resource availability information in a database accessible using the first device;
receiving a resource availability query from the second device using a network, the resource availability query including a resource specification;
identifying resource availability data from the collected resource availability information based on the resource specification;
aggregating the identified resource availability data; and
sending the aggregated resource availability data to the second device.

2. The method of claim 1, wherein collecting resource availability information comprises receiving the resource availability information from a third device associated with a first medical facility.

3. The method of claim 2, wherein collecting resource availability information further comprises sending a request to the third device, the request requesting resource availability data associated with the first medical facility.

4. The method of claim 2, wherein collecting resource availability information further comprises parsing the received resource availability information into a format compatible with the database.

5. The method of claim 1, wherein the resource specification identifies a region.

6. The method of claim 5, wherein the region is selected from the group consisting of a medical facility, a hospital system, a town, a city, a county, a state, a country, a federal emergency management agency region, and a center for disease control region.

7. The method of claim 1, wherein the sent aggregated resource availability data is formatted to support a hospital availability exchange guideline or a hospital available beds in emergencies and disasters specification, and wherein the resource availability information is stored in the database based on a hospital availability exchange guideline or a hospital available beds in emergencies and disasters specification.

8. The method of claim 1, wherein identifying resource availability data comprises querying the database based on the resource specification and receiving a result from the query.

9. The method of claim 8, wherein the resource availability query further includes a resource type and querying the database is further based on the resource type.

10. The method of claim 9, wherein the resource type is selected from the group consisting of an ambulance availability, a medical personnel availability, a medical equipment availability, a shelter availability, an emergency equipment availability, a bed availability, and a facility capacity.

11. The method of claim 9, wherein aggregating the identified resource availability data comprises summing the identified resource availability data based on the resource type.

12. The method of claim 1, wherein the resource availability query is received in a format defined based on a hospital availability exchange guideline or a hospital available beds in emergencies and disasters specification.

13. The method of claim 1, further comprising deriving a performance metric based on the collected resource availability information.

14. The method of claim 1, further comprising sending the collected resource availability information to a third device.

15. The method of claim 14, wherein the sending the collected resource availability information to the third device is performed in response to receiving a request from the third device to send the collected resource availability information.

16. The method of claim 1, wherein the resource availability query further includes a region identifier associated with the second device wherein identifying the resource availability data is further based on a comparison between the region identifier and a region list associated with the resource availability data.

17. The method of claim 1, wherein the resource availability query further includes a user identifier associated with a user of the second device wherein identifying the resource availability data is further based on a comparison between the user identifier and a user list associated with the resource availability data.

18. The method of claim 17, wherein identifying the resource availability data is further based on an evaluation of a time frame allocated to the user.

19. The method of claim 1, wherein the resource availability query further includes an emergency event identifier associated with the second device wherein identifying the resource availability data is further based on a comparison between the emergency event identifier and an emergency event list associated with the resource availability data.

20. The method of claim 1, further comprising, before identifying the resource availability data, comparing client information associated with the second device with resource access information, wherein identifying the resource availability data is further based on the comparison.

21. The method of claim 1, wherein the selectively polling the one or more resource stores associated with the plurality of medical facilities is performed in response to the received resource availability query from the second device.

22. The method of claim 1, wherein the selectively polling the one or more resource stores associated with the plurality of medical facilities is performed periodically according to a user-defined schedule.

23. The method of claim 1, wherein the selectively polling the one or more resource stores associated with the plurality of medical facilities is performed automatically in response to a change in the resource availability information.

24. The method of claim 1, wherein the selectively polling the one or more resource stores associated with the plurality of medical facilities is performed in response to a request received at the first device.

25. The method of claim 2, wherein the resource availability information includes a medical facility identifier associated with a medical resource.

26. A device comprising:
  a processor;
  a communication interface configured to send and to receive information from a network; and
  a computer-readable medium including computer-readable instructions stored therein that, upon execution by the processor, perform operations comprising
    collecting resource availability information from a plurality of medical facilities, wherein the collecting the resource availability information comprises selectively polling one or more resource stores associated with the plurality of medical facilities, wherein the selectively polling the one or more resource stores associated with the plurality of medical facilities is performed:
in response to the received resource availability query from the second device,
periodically according to a user-defined schedule, or
automatically in response to a change in the resource availability information;
storing the collected resource availability information in a database;
receiving a resource availability query from a second device, the resource availability query including a resource specification;
identifying resource availability data based on the resource specification;
aggregating the identified resource availability data; and
sending the aggregated resource availability data to the second device.

27. A non-transitory computer-readable medium including computer-readable instructions stored therein that, upon execution by a processor, cause the processor to provide resource availability information related to medical facilities to a second device in a network, the instructions configured to cause a computing device to:

collect resource availability information from a plurality of medical facilities using the network, wherein the collecting the resource availability information comprises selectively polling one or more resource stores associated with the plurality of medical facilities, wherein the selectively polling the one or more resource stores associated with the plurality of medical facilities is performed:
in response to the received resource availability query from the second device,
periodically according to a user-defined schedule, or
automatically in response to a change in the resource availability information;
store the collected resource availability information in a database;
receive a resource availability query from the second device using the network, the resource availability query including a resource specification;
identify resource availability data based on the resource specification;
aggregate the identified resource availability data; and
send the aggregated resource availability data to the second device using the network.

* * * * *

UNITED STATES PATENT AND TRADEMARK OFFICE
CERTIFICATE OF CORRECTION

| | | |
|---|---|---|
| PATENT NO. | : 8,428,961 B2 | Page 1 of 1 |
| APPLICATION NO. | : 11/895705 | |
| DATED | : April 23, 2013 | |
| INVENTOR(S) | : Greischar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

Signed and Sealed this
Sixteenth Day of December, 2014

Michelle K. Lee
*Deputy Director of the United States Patent and Trademark Office*